(12) United States Patent
Brown et al.

(10) Patent No.: US 11,718,817 B2
(45) Date of Patent: Aug. 8, 2023

(54) COMPOSITIONS AND METHODS FOR DISAGGREGATION OF BIOLOGICAL TISSUE SAMPLES

(71) Applicant: CLAREMONT BIOSOLUTIONS LLC, Upland, CA (US)

(72) Inventors: Mark Brown, Pasadena, CA (US); Robert Doebler, Upland, CA (US); Gary Fife Blackburn, Glendora, CA (US)

(73) Assignee: CLAREMONT BIOSOLUTIONS LLC, Upland, CA (US)

( * ) Notice: Subject to any disclaimer, the term of this patent is extended or adjusted under 35 U.S.C. 154(b) by 0 days.

(21) Appl. No.: 17/706,101

(22) Filed: Mar. 28, 2022

(65) Prior Publication Data

US 2023/0042117 A1 Feb. 9, 2023

Related U.S. Application Data

(63) Continuation of application No. 17/014,786, filed on Sep. 8, 2020, now Pat. No. 11,286,447, which is a continuation of application No. 15/566,158, filed as application No. PCT/US2016/027291 on Apr. 13, 2016, now Pat. No. 10,801,001.

(60) Provisional application No. 62/146,876, filed on Apr. 13, 2015.

(51) Int. Cl.
*C12M 1/00* (2006.01)
*C12M 3/08* (2006.01)
*C12M 1/33* (2006.01)

(52) U.S. Cl.
CPC ............ *C12M 3/08* (2013.01); *C12M 45/02* (2013.01); *F05D 2250/82* (2013.01); *F05D 2270/03* (2013.01)

(58) Field of Classification Search
None
See application file for complete search history.

(56) References Cited

U.S. PATENT DOCUMENTS

| 6,392,313 B1 | 5/2002 | Epstein et al. |
| 2007/0148756 A1* | 6/2007 | Bullen ............... C12M 45/02 435/308.1 |

OTHER PUBLICATIONS

International Search Report and Written Opinion, dated Jul. 26, 2016, for International Application No. PCT/US16/27291, 8 pages.

* cited by examiner

*Primary Examiner* — Jyoti Nagpaul
(74) *Attorney, Agent, or Firm* — Seed Intellectual Property Law Group LLP

(57) ABSTRACT

Devices and methods for the efficient disaggregation of tissue samples, separating the tissue into individual intact cells or small aggregates of cells for analysis. A device may include a chamber to receive fluid and a tissue specimen containing more than one cell to be disaggregated. The chamber may include an opening and an agitator in fluid contact with the fluid and the tissue specimen. The agitator may include a micromotor which provides rotational motion to a shaft and an impeller fixed to the shaft such that the impeller and the shaft rotate together upon provision of the rotational motion by the micromotor. The device may include an electrical energy source electrically coupled to the micromotor to rotate the impeller sufficient to disaggregate the one or more individual cells from the tissue specimen and in a manner which does not lyse the one or more individual cells.

20 Claims, 5 Drawing Sheets

Disaggregated Sample
(10x magnification)

1:20 dilution
(10x magnification)

1:20 dilution
(40x magnification)

5 days
(40x magnification)

Stained with Trypan Blue

A. Disaggregated Chicken Heart Tissue (10x magnification)

B. Disaggregated Chicken Heart Tissue, 20x dilution (10x magnification)

C. Disaggregated Chicken Heart Tissue, 20x dilution (40x magnification)

D. Disaggregated Chicken Heart Tissue, 20x dilution, Trypan Blue Stained (40x magnification)

COMPOSITIONS AND METHODS FOR DISAGGREGATION OF BIOLOGICAL TISSUE SAMPLES

BACKGROUND

Technical Field

The present disclosure relates to preparation of samples for single-cell analysis. Analysis of multi-celled samples, e.g., tissue samples, requires that the cells be separated from one another if single cell analysis is desired. The present disclosure describes devices which aid in such tissue disaggregation or tissue dispersion. The present disclosure also relates to methods and devices for the lysis of cells and extraction of DNA in a cell for suitable for long-read sequencing and molecular combing analysis.

Description of the Related Art

The biology of cells is typically examined in cell monolayer culture applications, however, they have inherent limitations for studying the effects of and screening for drugs and predicting in vivo physiological responses (Girard et al., 2013, PLoS ONE, 8 (10):e75345). As is known in the art, in vitro single cells or cell monolayer behave very differently from an in vivo organization of cells, wherein the cells are organized in a sophisticated cellular network and form tissues. In those networks, cellular responses of individual cells to drugs may be, at least to a certain extent, controlled by its extracellular environment within such network or tissue. Such extra-cellular environment, for example, includes cell-cell interaction and cell-matrix interactions. Particularly, cell-matrix interactions play an important role in the formation of tumors and progression of tumors.

Tumor cell aggregates are believed to exhibit specific characteristic traits of their in vivo tumor counterparts. Through their more realistic demonstration of a tumor's in vivo architecture, cell-cell interactions and cell-matrix interactions, they provide more valuable information regarding the cellular differentiation, proliferation, apoptosis and gene expression of the tumor cells in question (Kim et al., 2004, Breast Cancer Research and Treatment, 85:281-291). Additionally, the use of tumor cell aggregates or tumor spheroids in drug screening assays allows one to observe the important interactions and behaviors of different cell types, and in particular, stroma cells.

For the reasons discussed above, it is particularly desirable to provide for drug validation and drug screening assays using cell aggregates or tissue fragments, which mimic more the physiological environment from where they are obtained than single cells. As such, there is a long felt need in the art to provide compositions and methods for the preparation of cell aggregates and/or tissue fragments which more accurately reflect the in vivo structure of a tissue, and more specifically, the in vivo structure of a cancerous tissue. The present disclosure provides compositions and methods useful for the processing of tissues and for the generation of a plurality of cells, a plurality of cell aggregates and/or tissue fragments. Tissues processed according to the present disclosure can be used in various assay systems, including, but not limited to, drug validation assays, drug screening assays, proliferation assays, metabolic assays, metastasis assays, angiogenesis assays, binding assays, biochemical assays, cellular assays, genetic assays, and the like.

Cancer is the second leading cause of death in the Western World, but is rapidly rising worldwide and is expected to become the number one killer in a few years. Thus, there is tremendous need to improve our understanding and ability to treat this deadly disease. Nearly all cancer types form solid tumors, abnormal tissue masses that are highly complex and dynamic. Recent evidence has pointed to a model in which tumors can be viewed as an ecosystem including a diverse array of cell types that work in concert to maintain homeostasis and drive further development. This intra-tumor cellular heterogeneity has been identified as a key factor underlying progression, metastasis, and the development of drug resistance. Cell types can include neoplastic subpopulations with distinct genotypes and phenotypes that are generated through clonal evolution, differentiation from rare stem-like precursors/cancer stem cells, or most likely a combination of the two mechanisms. Host cells of diverse origins, including non-tumor epithelium, stroma, and immune subtypes, can also assist the tumor in different capacities. Thus, analyzing tumor heterogeneity and identifying the presence of key cell types have become major focus areas in tumor biology and clinical diagnostics. Knowledge of different cell types can also drive patient-specific protocols for cancer treatment.

A major challenge for solid tumor analysis is the fact that specimens are three-dimensional tissue structures. This is particularly true to assessing cellular heterogeneity and identifying rare cell types such as cancer stem cells. Tissue-based analysis methods such as histology, immunohistochemistry, and fluorescence in-situ hybridization are clinical standards that provide morphological and sub-cellular detail, but are low throughput and detection signals are difficult to quantitate and multiplex. Techniques that involve sample destruction such as genome/transcriptome sequencing, microarrays, mass spectrometry, and Western blotting can provide large amounts of molecular information but retain no context with respect to the cellular components in the original sample. Due to these limitations, researchers and clinicians are increasingly employing cell-based analysis platforms such as flow cytometry because they offer high-throughput and multiplexed information about each cell within the sample. Cell sorting can also be used to isolate rare cell types such as cancer stem cells, metastatic precursors, and drug resistance clones for additional study. The disadvantage is that the tissue must first be broken down into single cells, which requires considerable expenditure of time and effort. Moreover, dissociation can potentially damage or otherwise bias samples. Thus, tissue dissociation remains a major barrier to the application of single cell techniques to solid tumor specimens.

Tumor tissue is currently dissociated into single cells using proteolytic enzymes that digest cellular adhesion molecules and/or the underlying extracellular matrix. The tumor tissue specimen is first minced with a scalpel into approximately 1-2 mm pieces. The enzyme or enzyme cocktail of choice is then applied. Trypsin is a broadly reactive protease that is highly efficient, requiring only short incubation times on the order of 15 minutes. Unfortunately, trypsin can also cleave cell surface proteins that may provide important diagnostic information or regulate cell function. For example, it has been shown that CD44, a commonly used cancer stem cell marker, is cleaved by trypsin resulting in significantly reduced expression. Collagenase is a milder alternative that digests collagen within the underlying extracellular matrix, leaving cells largely undisturbed. For this reason, collagenase has been employed for identifying and isolating cancer stem cells via CD44 or other biomarkers. However, collagenase requires long incubation times on the order of 1 to 2 hours that could negatively affect cell viability or molecular expression. Non-enzymatic options such as the calcium chelator ethylenediaminetetraacetic acid (EDTA) can also be employed, but EDTA is much less efficient and therefore used only to augment protease digestion. Following initial enzymatic or chemical treatment procedure, samples are subjected to fluid shear forces to mechanically liberate individual cells. This is typically achieved by vortexing and/or repeatedly pipetting the sample. These methods generate poorly defined shear flow environments that do not allow control over sample exposure, potentially resulting in variations across different batches or laboratories. The gentleMACS™ Dissociator (Miltenyl Biotec) is a commercial system that has been developed to standardize mechanical dissociation, but its use with tumor specimens is not common and performance is not well documented.

A final step that is used in many dissociation processes is to remove large aggregates that remain by filtering, which results in loss of sample. Taken together, tumor tissue dissociation involves multiple manual processing steps that are time-consuming and labor intensive, and there are numerous areas for which the resulting cell suspension can be improved. Notably, enzymatic digestion is either harsh or very long, large aggregates are lost to filtering, and there is no way to control whether the recovered sample contains single cells versus small clusters. Thus, new technology and methodology development is critically needed to meet all of the following goals: (1) improve dissociation efficiency so that the entire sample is recovered as single cells, (2) maximize overall cell quality in terms of viability and molecular biomarker expression, (3) decrease processing time from hours to minutes, and (4) automate the entire workflow to enable point-of-care operation and direct connection to additional downstream tasks.

BRIEF SUMMARY

There is a need for methods and devices to provide rapid and simple disaggregation of tissue and/or cell aggregates to produce suspensions of individual cells to allow for analysis of cells independently.

For example, cancer tissue is generally a heterogeneous population of several types of cells, often at different stages of progression. There is a need for better methods and devices to allow such cancer tissues to be separated from one another for analysis. The individual cells may be examined visually using a microscope. Often such cells are stained by any of many techniques known in the literature in order to determine particular characteristics of the cells. Often, the cells are classified and counted as a means of characterizing the cancer tissue. Such could not be readily performed unless the tissue was disaggregated.

Another method for characterizing a cancer tissue by characterizing the individual cells of the tissue involves performing nucleic acid sequencing of individual cells from the population. Such methods allow the heterogeneity of the tissue to be better understood and can be used to target particular treatment strategies dependent upon the characteristics of the tissue.

Individual cells can also be characterized by performing reverse-transcriptase PCR of mRNA in the cell and determining the gene expression level for genes or sequences of interest. Often, nucleic acid microarray techniques are employed to measure the relative concentration of many different mRNAs. Compilation of such information for many individual cells of a particular cancer tissue provides invaluable information to aid, for example, physicians to apply more optimal treatment to the patients.

Tissue of various types can also be characterized by disaggregating the tissue and then analyzing individual cells by flow cytometry. In such techniques, labeled nucleic acid probes, labeled antibodies, and stains are often used, sometimes simultaneously, to allow more specific characterization of each cell type and the population density of each cell class.

Techniques such as those described, as well as many others known to those skilled in the art, all benefit from the ability to effectively separate the cells of a tissue into individual cells. Beneficially, the methods for disaggregation should be relatively indiscriminate as to cell type so that the population of released cells is representative of the population of the original tissue. Methods and devices to disaggregate tissue should also do so with as little damage or change to the morphology of the cells so that their properties are as similar as practical to their state in the tissue. It is also important form most analysis techniques that the cell membranes of the cells be kept intact, i.e., the cells are not lysed to any great extent, to allow more accurate analysis of the biomolecules inside the cell membrane. Further, when the tissue is fresh and the tissue cells are living, it is often important that the disaggregation methods do not kill the cells to any appreciable extent.

Described herein are methods and devices which provide rapid and simple disaggregation of tissue sample or of multicellular specimens of biological material.

In general, the methods described herein use novel devices which incorporate micromotors to provide mechanical energy to fluids containing the tissue specimens. Such micromotors are commonly employed in cell phones to provide vibration of the phone. Such micromotors are also commonly employed in toys and robotic devices, for example, in model helicopters and model boats. The micromotors are generally operated by application of a dc voltage to the terminals of the micromotor. Most applications of the micromotors are for battery powered devices and the micromotors are, therefore, generally designed to operate at a voltage of 1.5 volts or greater. The micromotors are generally cylindrical in shape and usually have a diameter of less than 15 millimeters (mm). Because the micromotors are small, they generally co not deliver very much torque, but do rotate at very high rate. Rotation of up to 50,000 revolutions per minute (rpm) or greater are possible. The rotation speed of the micromotors is generally dependent on the voltage applied. Most applications, however, use the micromotors at the upper end of their speed rating and, thus, at the upper end of their recommended voltage specification. Because the motors are designed and manufactured to operate at high rotational speeds, they typically provide only low torque. As a consequence, the motors may not begin to turn if the shaft extending from the cylindrical body is in contact with another object. Similarly, the motors stop turning easily if the shaft makes contact with another object.

Because of the low torque nature of micromotors, there can be no significant seal mechanism around the shaft to keep fluids from entering the body of the motor. All attempts to encircle the shaft with a fluid barrier such as a grommet or O-ring have resulted in significantly reduced speeds, or more commonly, inability to turn on the motor to rotate.

In some implementations of the present disclosure, the motors are used in direct contact with the fluid and/or tissue specimen, hence, without any fluid barrier to impede the rotation of the shaft and impeller. This configuration allows the motor to operate at high RPMs to drive the shaft and impeller at high speed. Surprisingly, the motors continue to operate in direct contact with the fluid.

In one or more implementations of the present disclosure, the shaft and metal of the motor are treated with a silane compound such as HMDS (hexamethyldisilizane) or alkylsilane. As is understood by those skilled in the art, such treatment causes a reaction between the silane and the metal surface to form a very thin layer on the surface of the metal. In general, it was found that treatment with hydrophobic silanes such as HMDS or alkylsilane impedes the penetration of fluid into the motor body and thus improves the performance of the motor in direct contact with the fluid. It is assumed that the silane treatment forms a hydrophobic barrier and that the high surface tension of water does not allow it to pass the narrow passage between the shaft and the motor body.

Disaggregation of multicellular specimens is often also referred to as dispersion or separation. These terms are used interchangeably in this description.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

Figure 1:
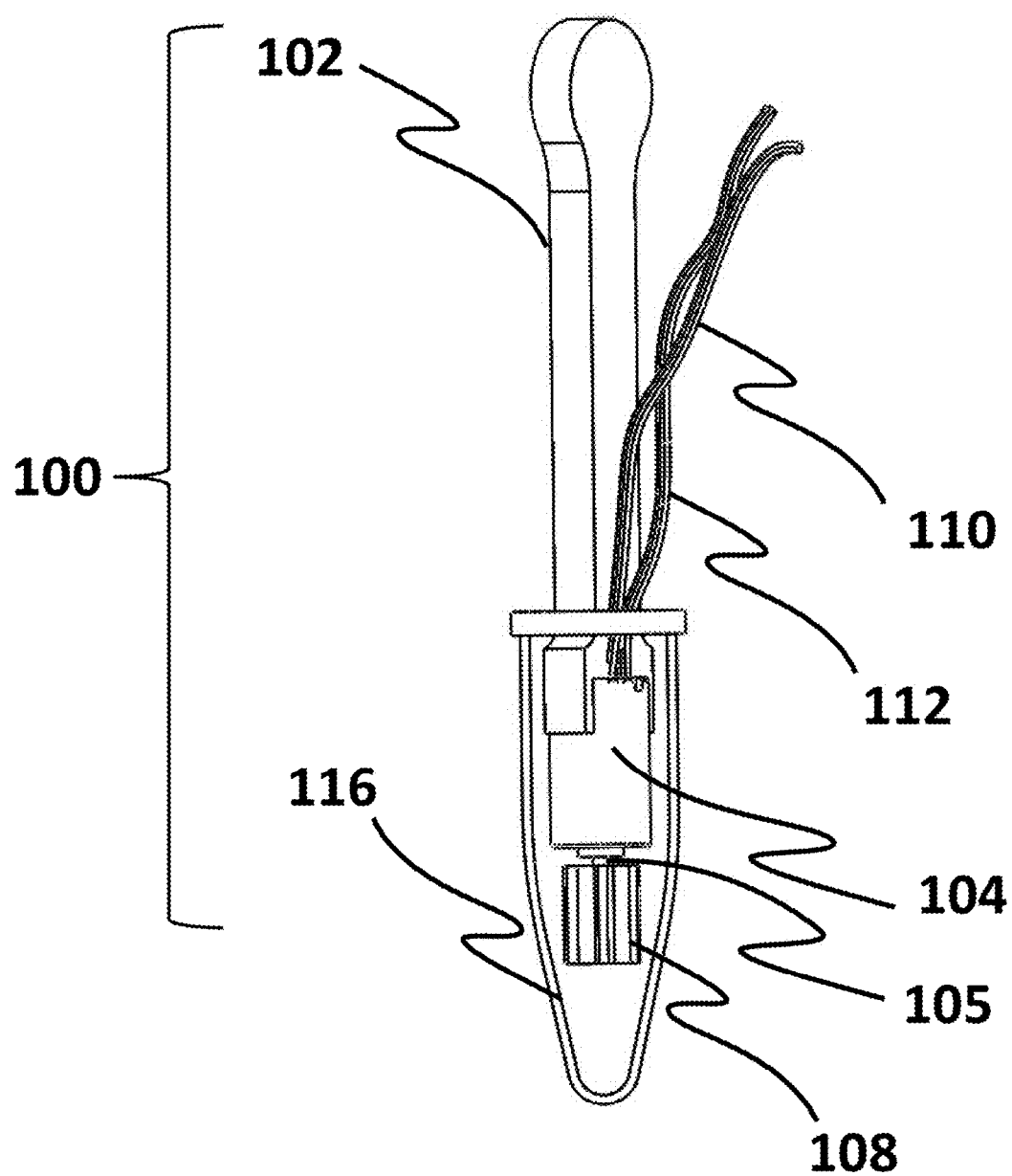
FIG. 1 is a schematic view of a disaggregation apparatus comprising an agitator and a container, according to one illustrated implementation.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with computer systems, server computers, and/or communications networks have not been shown or described in detail to avoid unnecessarily obscuring descriptions of the implementations. In other instances, methods commonly known for use with and manipulation of tissue, cells, nucleic acids, proteins, polypeptides, and other biological materials have not been described, as they would be readily available to those of ordinary skill in the art of such materials.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the context clearly dictates otherwise. It should also be noted that the term "or" is generally employed in its sense including "and/or" unless the context clearly dictates otherwise.

The headings and Abstract of the Disclosure provided herein are for convenience only and do not interpret the scope or meaning of the implementations.

A number of implementations of disaggregation apparatus, systems and methods of use are described herein. The disaggregation apparatus and systems perform disaggregation on a tissue using mechanical agitation, to produce single cells. The material to be disaggregated may take the form of solid biological materials, for example cancer biopsies, cancer tissue, normal tissue, blood, cervical swab samples, plant tissue, formalin-fixed, paraffin-embedded (FFPE) samples, fresh frozen samples, fine needle aspirate samples, etc.

In one general implementation, the disaggregation apparatus includes a container such as a micro-centrifuge tube and an agitation device. The agitation device is sized so that a portion of it can be inserted into the opening of the container and comprises a micromotor having a shaft at one end and an impeller fitted on the end of the shaft. The micromotor can be connected to a voltage or current source to drive the micromotor.

To perform disaggregation, the tissue to be disaggregated is placed in the container, generally with a fluid such as saline that is compatible with the tissue and cells of the tissue. The agitation device is then partially inserted into the opening in the container such that the impeller is submerged in the fluid. At least a portion of the micromotor is exposed to the fluid and tissue during operation. The micromotor is then connected to a voltage or current source such that the motor shaft and impeller turn. The operator applies sufficient voltage or current to mechanically agitate the tissue such that single cells are disaggregated from the tissue sample. Following sufficient disaggregation, the motor is disconnected from the power source and the agitator device is removed from the opening of the container. The fluid can then be removed from the container, for example with a syringe or pipettor, and the fluid, which contains the disaggregated single cells, can be transferred to another container and then analyzed.

In some implementations, particulate material may be added to the container. Such particulate material, e.g., ceramic or glass beads, may aid in the mechanical disaggregation of the tissue sample.

The particulate material may take a variety of forms. While often referred to herein as beads, the term bead is not meant to be limiting with respect to size or shape. The beads may, for example, comprise ceramic, glass, zirconia, zirconia/silica, zirconium silicate, metal, plastic, nickel, tungsten, tungsten carbide, yttrium stabilized zirconia, sand, and/or particles of any geometry such as shard or of random shape.

In a first implementation, the disaggregation apparatus comprises a container and an agitator comprising a micromotor attached to a handle which may be comprised of plastic, metal, or any of a variety of other solid materials. The micromotor is largely cylindrical in shape having a shaft protruding from one of the ends of the cylinder. The micromotor has two or more electrical wires attached to supply power to the micromotor to induce the motor and shaft to turn. The handle is mounted or attached to the end of the micromotor opposite the end from which the shaft protrudes. The handle is generally from one to three inches in length and provides a means to handle the agitator conveniently. Attached to the shaft of the micromotor is an impeller. The impeller generally has blade-like protrusions from its generally cylindrical shape. The blade-like protrusions may be of a wide variety of shapes and geometries and generally aid in the transfer of mechanical energy from the impeller to a fluid surrounding the impeller. The disaggregation device further comprises a container having one opening having a diameter slightly larger than the diameter of the micromotor so that the micromotor may be slidingly engaged into the opening. In some implementations, the container is a microcentrifuge tube. The volume of the container is generally in the range of 0.5 to 5 mL and more preferable 1 to 3 mL, for example.

In operation, this disaggregation apparatus is used by inserting a tissue sample and a fluid into the container and then inserting the agitator micromotor into the opening in the container such that the impeller is immersed in the fluid. A voltage or voltage waveform is applied to the wire leads which induce a rotational motion of the impeller which induces a turbulent rotational movement in the fluid and tissue. The voltage or voltage waveform is applied for a period of time sufficient to disaggregate the tissue into a suspension of intact individual cells or small aggregates of cells without causing substantial lysis of the cells of the tissue.

FIG. 1 shown one implementation of the disaggregation apparatus described above. The handle 102 is attached to one end of the micromotor 104. The shaft 105 protrudes from the micromotor and an impeller 108 is attached to the shaft. Wire leads 110 and 112 are attached to the motor to allow the application of a voltage or voltage waveform to the micromotor. The leads are generally attached to a connector (not shown) to allow simple attachment to the voltage source. One lead, 110 is designated as negative and the other lead, 112, is designated positive. When attached to a battery having negative and positive terminals attached to the negative 110 wire lead positive wire leads, respectively, the motor shaft and impeller will rotate in, for example a clockwise direction. If the two wire leads are reversed, the rotation of the shaft and impeller will be counter-clockwise. Application of a voltage waveform such as a sine wave, triangle wave, square wave, or more complex waveforms will result in changes in the rotation speed and direction. The container 116 surrounds the micromotor and impeller. In use the fluid and tissue fill the space in the container 116 surrounding the impeller and in contact with the micromotor body.

The disaggregation apparatus or device of the type shown in FIG. 1 having an agitator comprising a handle and a micromotor and impeller has dimensions which are small in comparison to prior art devices for other applications which may comprise a motor and a handle. For example, the dimensions of the device of FIG. 1 are preferably only 25 to 75 mm in height and 5 to 15 mm in width. Such small dimension is fortuitous in that the device may be used to disaggregate small tissue samples using containers that have a small (0.5 to 3 mL) volume.

The micromotors of the present disclosure are of the types that are commonly used in cell phones to provide vibration alerts to the user. The micromotors of the present disclosure are typically 4 mm to 7 mm in diameter but can have diameters in the range of 3 mm to 10 mm, for example. Such micromotors work surprisingly well in this application because they are small enough to fit into standard microcentrifuge tubes. Further, the micromotors are able to operate at a high speed (typically 20,000 to 50,000 rpm maximum speed) in direct contact with fluid for a length of time sufficient to perform disaggregation of tissue. The micromotors are also advantageous in that they can be operated using batteries as the voltage source since they draw only, for example, 20 to 100 mA of current. Further, the micromotors are inexpensive enough that the entire apparatus can be disposable after a single use or after multiple uses.

In another preferred implementation, the disaggregation apparatus comprises a container having a first opening for the introduction of tissue and fluid and a second opening in which the micromotor is sealingly engaged. The second opening is generally at the bottom of the container such that gravity will pull the tissue and fluid into contact with the micromotor, shaft, and impeller. This apparatus generally has a base to support the opposite end of the micromotor and thereby support the entire disaggregation apparatus. A lid for the container is generally fitted into the first opening during the disaggregation procedure so the fluid and tissue remain in the container. Mounted on the shaft of the micromotor is an impeller. Electrical leads or wires are connected to the micromotor to supply a voltage or voltage waveform to induce the shaft and impeller to rotate.

Figure 2:
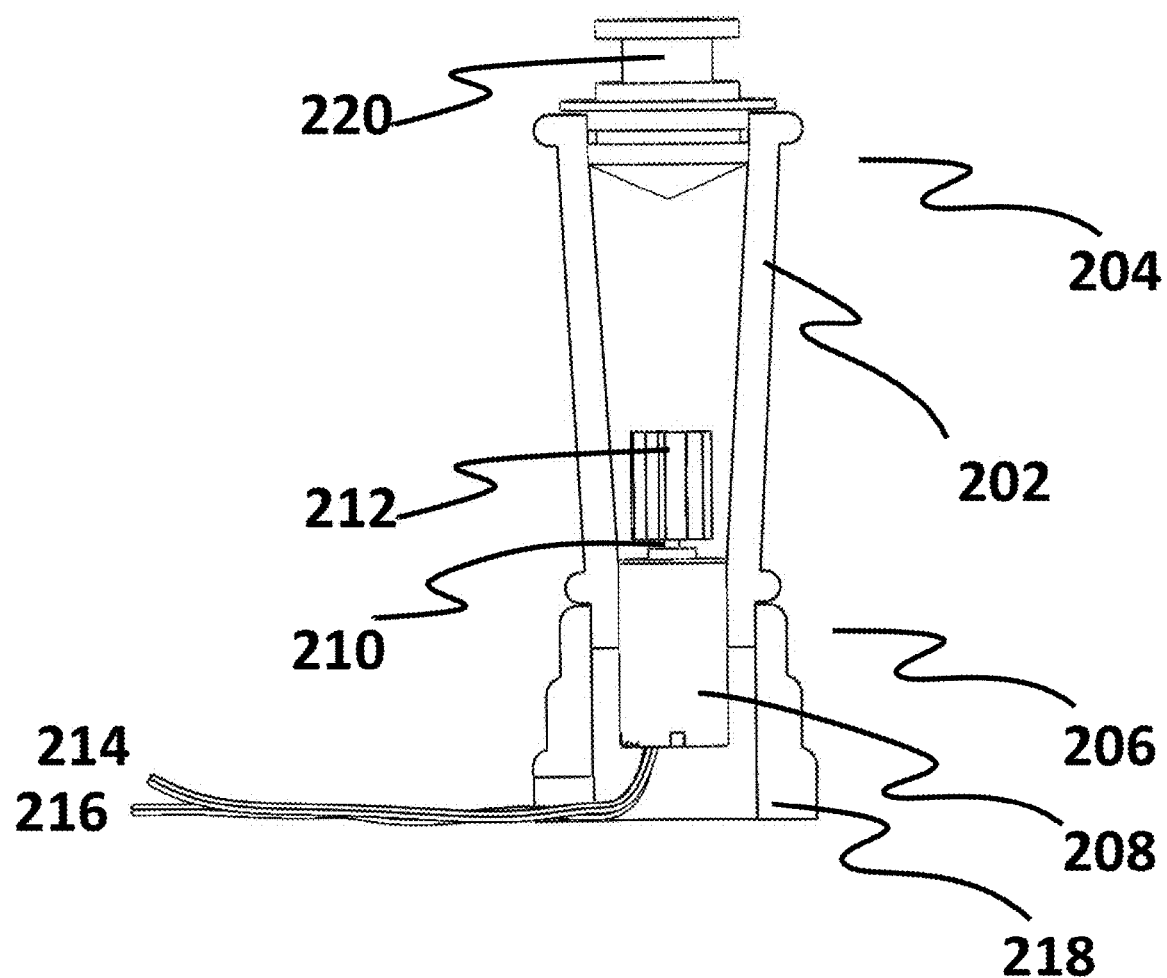
FIG. 2 is a schematic view of a disaggregation apparatus comprising an integrated container and agitator, according to one illustrated implementation.

FIG. 2 shows another implementation of the apparatus or device. The apparatus comprises a container 202 having a first opening 204 and a second opening 206. A micromotor 208 is sealingly engaged in the second opening 206 of the container 202. Protruding from the one end of the micromotor is a shaft 210 upon which is mounted an impeller 212. Electrically attached to the micromotor 208 are two electrical leads or wires 214 and 216. The container 202 is mounted in a solid base 218 which may be plastic or metal or another solid material. In some implementations a permanent magnet is mounted in the bottom of the base (not shown) to facilitate holding of the apparatus on a ferromagnetic base plate (not shown). The first opening 204 of the container 202 is optionally closed with a removably and sealingly engaged cap 220 which seals the container during use to contain a fluid and tissue during the disaggregation process.

The disaggregation apparatus in its various implementations may be combined with additional such devices in an array of devices to form an apparatus for the disaggregation of multiple tissue samples simultaneously of serially. For example, the agitator 100 of FIG. 1 may be combined with other such devices in a linear array device of eight or twelve with a 9 mm spacing such that the linear array disaggregation device can be used to disaggregate eight or twelve tissue samples in, for example, one row or one column of a standard 96-well plate. In such an implementation, the plate replaces the individual container of FIG. 1, serving as a 96-well container. The 96-well plate in one implementation is a deep-well plate which better accommodates the depth of the multi-agitator when inserted into the plate for disaggregation without spillage of the tissue or fluid from the wells of the plate.

The disaggregation devices of the present disclosure, in many implementations, use a micromotor which is sealed with a plastic material or other material at the end opposite the shaft end of the micromotor. It was discovered that sealing the end of the micromotor facilitates operation of the micromotor in direct contact with the fluid which contains the tissue. With the non-shaft end of the motor sealed, the only opening to the interior of the micromotor is around the shaft of the motor. Sealing of the opposite end presumably helps to keep fluid from flowing into the interior of the micromotor which could ultimately cause electrical failure. In a test, it was shown that sealed micromotors can function for several hours in contact with saline whereas non-sealed micromotors only operated for a few minutes.

The devices of the intention are used to disaggregate tissue, in one implementation using the device of FIG. 1 by placing the tissue sample into the container. A buffer solution is also added to the container which may be standard saline of a pH buffered saline of any fluid compatible with the tissue and disaggregated cells. The fluid is of sufficient volume to fully surround the tissue sample. Then, the agitator is inserted into the container to a depth such that the impeller is surrounded, at least partially, with the fluid. A voltage or voltage waveform is then applied to the motor through the wire leads. The motor is activated and turns its shaft which in turn turns the impeller. The voltage or voltage waveform is applied for a time sufficient to disaggregate the tissue into intact single cells or multi-cell clusters suspended in the fluid. The time required is typically from 30 seconds to 5 minutes. The agitator is then removed from the container, leaving the disaggregated tissue cell suspension in the container.

In some implementations, the voltage applied to the micromotor may be important for efficient disaggregation of the tissue without causing significant lysis of the cells. It has been shown that a DC voltage can be employed where the voltage is usually less than the recommended operating voltage for the particular micromotor being used. For example, for a micromotor having a recommended operating voltage of 1.5 V, it was found that a DC voltage of 0.25 to 1.5 volts would effectively disaggregate tissue. In some implementations, voltages of 10% to 150% of the manufacturer recommended operating voltage is applied and in at least some implementations, a DC voltage of 25% to 75% of the manufacturer recommended operating voltage is employed.

In other implementations of the present disclosure, voltage waveforms are used to drive the micromotor. For example, if a square wave is employed having a center voltage of zero and an amplitude in the ranges described in the previous paragraph, the micromotor will turn first in one direction and then in the other direction. It is found that this waveform results in efficient tissue disaggregation for some tissue types. In other implementations, a sine wave or a triangle wave are used to drive the micromotor. Any of the waveforms may have a zero or non-zero center voltage and have an amplitude in the ranges described in the previous paragraph.

Figures 3A, 3B:
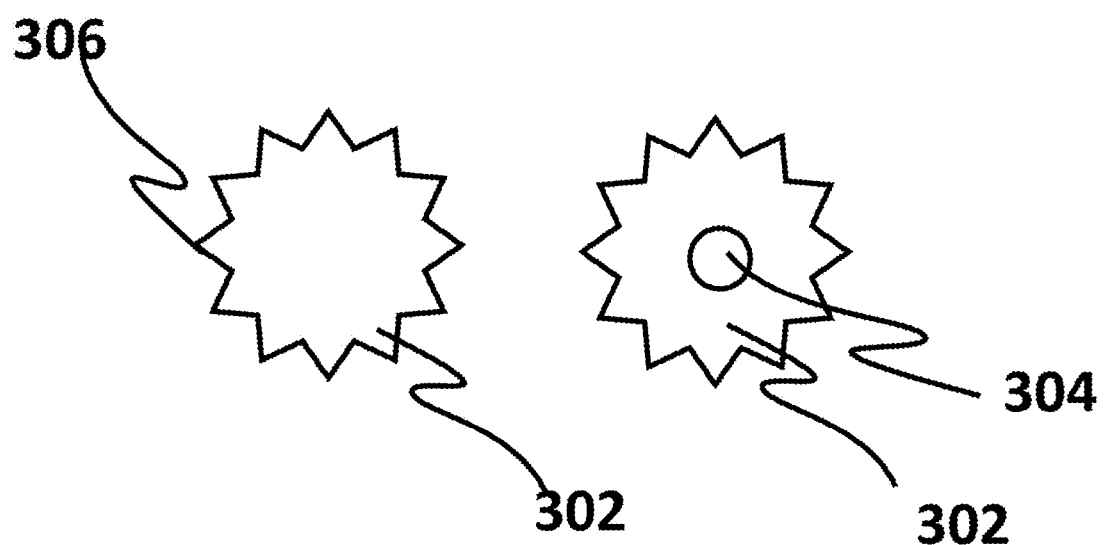
FIGS. 3a-3b are sectional views of an impeller used in one or more implementations of the present disclosure, according to one illustrated implementation.

The shape and dimensions of the impeller and container may also be important to the efficient disaggregation of tissue samples. It was found that an impeller in the shape of a cylinder having vanes protruding from its surface may be advantageous. FIG. 3a shows a cross section of an impeller 302 of one implementation of the present disclosure furthest from the shaft of the micromotor. FIG. 3b shows a cross section of the same impeller 302 near the end where the impeller is mounted on the shaft of the micromotor. A cylindrical cavity 304 in the center of the impeller facilities mounting of the impeller 302 on the cylindrical shaft of the micromotor (not shown). Around the circumference of the impeller are shown the vanes or blades 306 (only one numbered).

At least some of the implementations take advantage of the understanding that the forces responsible for mechanical disaggregation of biological samples such as tissue samples scale with the oscillation frequency squared, and that by employing relatively small sample sizes, the various implementations described herein can achieve relatively higher frequencies as well as lower frequencies than commercially available apparatus, resulting in rapid and efficient tissue disaggregation.

In at least one implementation of the present disclosure, the voltage source is integrated into the device. For example, for implementations similar to that in FIG. 1, a battery, preferably in the form of one or more button cells, may be included in the handle. Such integration results in a device that is easier to use by the end user. Further, the capacity of the voltage source may be limited to discourage the device to be used for multiple disaggregation procedures which can result in contamination by carryover of components of one tissue sample to later disaggregated tissue samples.

EXAMPLE 1

Disaggregation of Chick Embroyo Tissue

Figure 4:
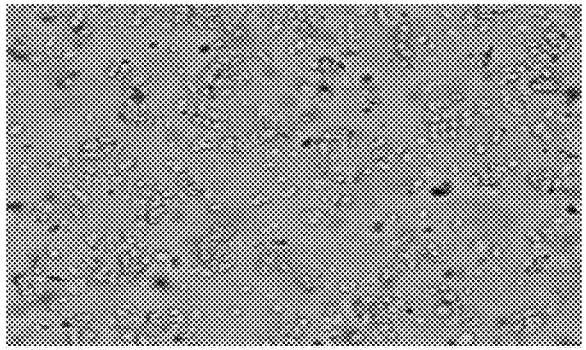
FIG. 4 shows photomicrographs of a disaggregated suspension of chick embryo tissue, according to one illustrated implementation.
Figure 4:
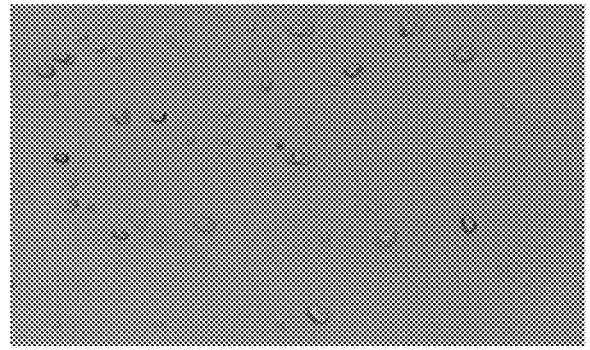
Figure 4:
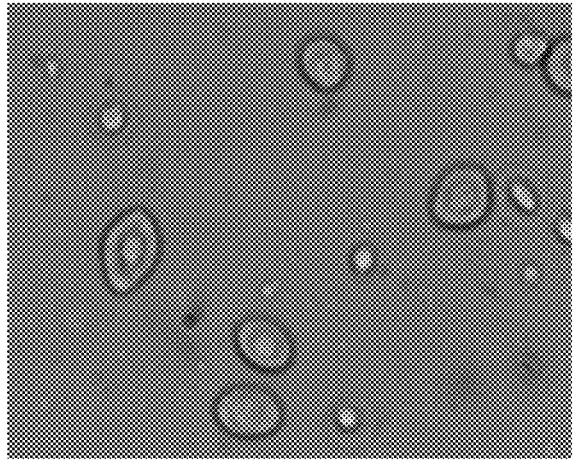
Figure 4:
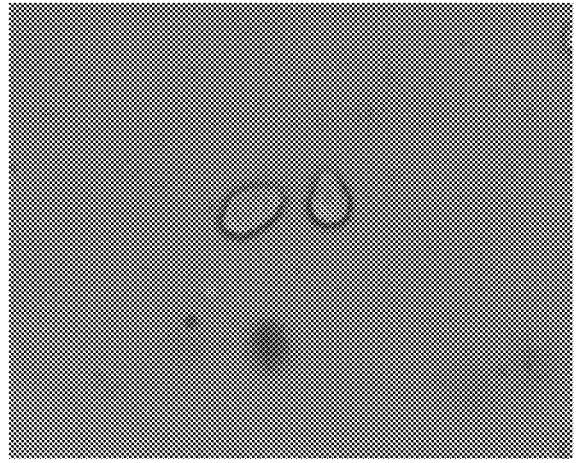

A small sample of chick embryo tissue was placed in phosphate buffered saline (PBS). The tissue and PBS were transferred to the disaggregation device of the type shown in FIG. 1. A DC voltage of 0.5 volts was applied to the micromotor for three minutes. The agitator was removed from the micro-centrifuge tube and the suspension was transferred to a clean tube and diluted with Hibernate® media (Gibco). FIG. 4 shows photomicrographs of the disaggregated suspension stained with Trypan Blue for visualization (10× magnification). Also shown are 1:20 dilutions of the cell suspension at both 10× and 40× magnification. The cell suspension was stored in a refrigerator for five days and was again observed under a microscope, as shown in the bottom right of FIG. 4. Shown in FIG. 4 is a photomicrograph showing that the cells remain healthy and intact.

EXAMPLE 2

Disaggregation of Chick Heart Tissue

Figure 5:
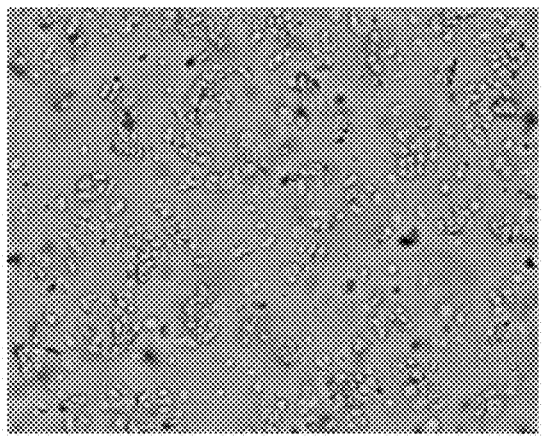
FIG. 5 shows photomicrographs of a disaggregated suspension of chick heart tissue, according to one illustrated implementation.
Figure 5:
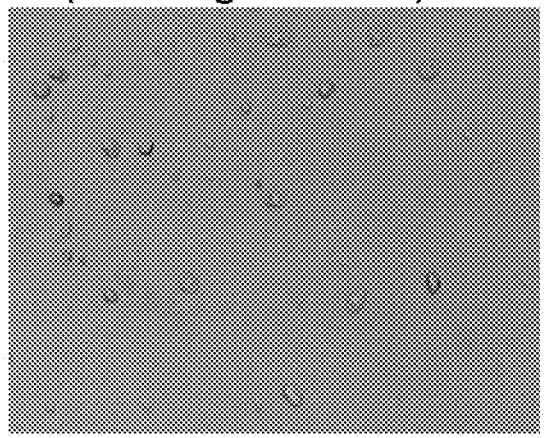
Figure 5:
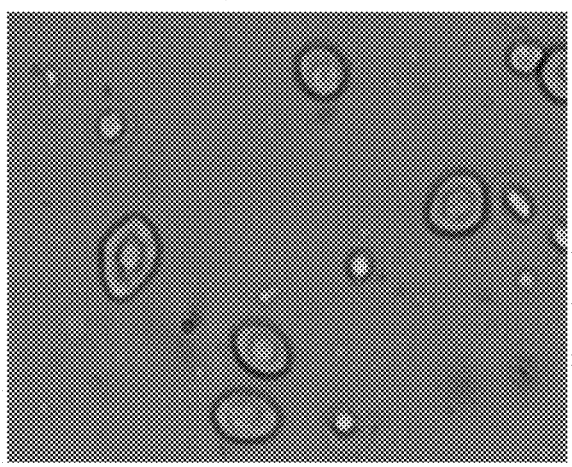
Figure 5:
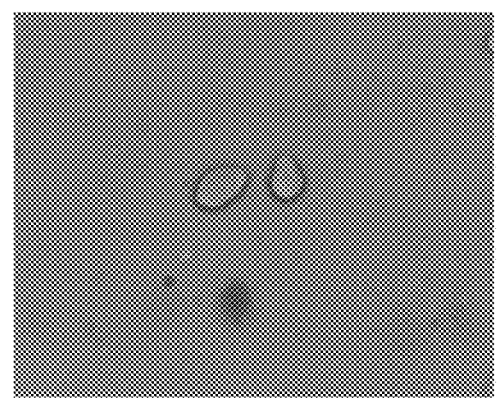

A small sample of chick heart tissue was placed in phosphate buffered saline (PBS). The tissue and PBS were transferred to the disaggregation device of the type shown in FIG. 1. A DC voltage of 0.5 volts was applied to the micromotor for three minutes. The agitator was removed from the micro-centrifuge tube and the suspension was transferred to a clean tube and diluted with Hibernate® media (Gibco). FIG. 5, frame A, shows a photomicrographs of the disaggregated suspension at 10× magnification prior to dilution. FIG. 5, frame B, shows a photomicrographs of the disaggregated suspension diluted 20:1 at 10× magnification. FIG. 5, frame C, shows a photomicrographs of the disaggregated suspension diluted 20:1 at 40× magnification.

FIG. 5, frame D, shows a photomicrographs of the disaggregated suspension diluted 20:1 at 40× magnification following Trypan Blue staining which stains only dead cells.

The various embodiments described above can be combined to provide further embodiments. U.S. Provisional Application 62/146,876, filed Apr. 13, 2015 is incorporated herein by reference, in its entirety. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method to release one or more individual cells from a multi-cellular tissue specimen to permit analysis of the one or more individual cells independently, the method comprising:
   placing the multi-cellular tissue specimen and a fluid in a chamber, the chamber comprising:
      at least a first opening to provide fluid communication with the chamber and to receive the tissue specimen; and
      an agitator in fluid contact with the fluid and the tissue specimen, the agitator comprising:
         a micromotor which provides rotational motion to a shaft extending from an interior of the micromotor, and
         an impeller fixed to the shaft such that the impeller and the shaft rotate together upon provision of the rotational motion by the micromotor,
      wherein at least a portion of the micromotor is removably received in the first opening of the chamber and forms a sealing arrangement to seal the first opening in use;
   applying electrical energy to the micromotor with an electrical energy source electrically coupled to the micromotor, the electrical energy sufficient to rotate the shaft and the impeller in a manner sufficient to disaggregate the one or more individual cells from the tissue specimen and in a manner which does not lyse the one or more individual cells;
   removing the one or more individual cells from the chamber; and
   performing nucleic acid sequencing of at least one of the disaggregated one or more individual cells.

2. The method of claim 1 wherein the multi-cellular tissue specimen comprises cancer tissue.

3. The method of claim 1 wherein applying the electrical energy comprises applying electrical energy sufficient to rotate the shaft and the impeller in a manner sufficient to disaggregate the one or more individual cells from the tissue specimen and in a manner which does not lyse more than 5% of the cells in the multi-cellular tissue specimen.

4. The method of claim 1 wherein applying the electrical energy comprises applying electrical energy sufficient to rotate the shaft and the impeller in a manner sufficient to disaggregate the one or more individual cells from the tissue specimen and in a manner which does not lyse more than 10% of the cells in the multi-cellular tissue specimen.

5. The method of claim 1 wherein applying the electrical energy comprises applying electrical energy sufficient to rotate the shaft and the impeller in a manner sufficient to disaggregate the one or more individual cells from the tissue specimen and in a manner which does not lyse more than 20% of the cells in the multi-cellular tissue specimen.

6. The method of claim 1 wherein applying the electrical energy comprises applying a DC voltage of less than 2.0 volts.

7. The method of claim 1 wherein applying the electrical energy comprises applying a DC voltage of less than 1.5 volts.

8. The method of claim 1 wherein applying the electrical energy comprises applying a DC voltage of less than 1.0 volts.

9. The method of claim 1 wherein applying the electrical energy comprises applying a DC voltage of less than 0.5 volts.

10. The method of claim 1 wherein applying the electrical energy comprises applying a voltage waveform selected from the group consisting of: a sine wave, a square wave, a triangle wave, and a combination of a sine wave, square wave, and a triangle wave.

11. A method to release one or more individual cells from a multi-cellular tissue specimen to permit analysis of the one or more individual cells independently, the method comprising:
   placing the multi-cellular tissue specimen and a fluid in a chamber, the chamber comprising:
      at least a first opening to provide fluid communication with the chamber and to receive the tissue specimen; and
      an agitator in fluid contact with the fluid and the tissue specimen, the agitator comprising:
         a micromotor which provides rotational motion to a shaft extending from an interior of the micromotor, and
         an impeller fixed to the shaft such that the impeller and the shaft rotate together upon provision of the rotational motion by the micromotor;
      wherein at least a portion of the micromotor is removably received in the first opening of the chamber and forms a sealing arrangement to seal the first opening in use;
   applying electrical energy to the micromotor with an electrical energy source electrically coupled to the micromotor, the electrical energy sufficient to rotate the shaft and the impeller in a manner sufficient to disaggregate the one or more individual cells from the tissue specimen and in a manner which does not lyse the one or more individual cells;
   removing the one or more individual cells from the chamber; and
   performing molecular combing analysis on at least one of the disaggregated one or more individual cells.

12. The method of claim 11 wherein the multi-cellular tissue specimen comprises cancer tissue.

13. The method of claim 11 wherein applying the electrical energy comprises applying electrical energy sufficient to rotate the shaft and the impeller in a manner sufficient to disaggregate the one or more individual cells from the tissue specimen and in a manner which does not lyse more than 5% of the cells in the multi-cellular tissue specimen.

14. The method of claim 11 wherein applying the electrical energy comprises applying electrical energy sufficient to rotate the shaft and the impeller in a manner sufficient to disaggregate the one or more individual cells from the tissue specimen and in a manner which does not lyse more than 10% of the cells in the multi-cellular tissue specimen.

15. The method of claim 11 wherein applying the electrical energy comprises applying electrical energy sufficient to rotate the shaft and the impeller in a manner sufficient to disaggregate the one or more individual cells from the tissue specimen and in a manner which does not lyse more than 20% of the cells in the multi-cellular tissue specimen.

16. The method of claim 11 wherein applying the electrical energy comprises applying a DC voltage of less than 2.0 volts.

17. The method of claim 11 wherein applying the electrical energy comprises applying a DC voltage of less than 1.0 volts.

18. The method of claim 11 wherein applying the electrical energy comprises applying a DC voltage of less than 0.5 volts.

19. The method of claim 11 wherein applying the electrical energy comprises applying a voltage waveform selected from the group consisting of: a sine wave, a square wave, a triangle wave, and a combination of a sine wave, square wave, and a triangle wave.

20. A method to release one or more individual cells from cancer tissue to permit analysis of the one or more individual cells independently, the method comprising:
   placing the cancer tissue and a fluid in a chamber, the chamber comprising:
      at least a first opening to provide fluid communication with the chamber and to receive the cancer tissue; and
      an agitator in fluid contact with the fluid and the cancer tissue, the agitator comprising:
         a micromotor which provides rotational motion to a shaft extending from an interior of the micromotor, and
         an impeller fixed to the shaft such that the impeller and the shaft rotate together upon provision of the rotational motion by the micromotor;
      wherein at least a portion of the micromotor is removably received in the first opening of the chamber and forms a sealing arrangement to seal the first opening in use;
   applying electrical energy to the micromotor with an electrical energy source electrically coupled to the micromotor, the electrical energy sufficient to rotate the shaft and the impeller in a manner sufficient to disaggregate the one or more individual cells from the cancer tissue and in a manner which does not lyse the one or more individual cells;
   removing the one or more individual cells from the chamber; and
   performing at least one of:
      nucleic acid sequencing of at least one of the disaggregated one or more individual cells; or
      molecular combing analysis on at least one of the disaggregated one or more individual cells.

* * * * *